(12) United States Patent
Weiman et al.

(10) Patent No.: US 12,220,323 B2
(45) Date of Patent: *Feb. 11, 2025

(54) EXPANDING INTERVERTEBRAL IMPLANTS

(71) Applicant: GLOBUS MEDICAL, INC., Audubon, PA (US)

(72) Inventors: Mark Weiman, Downingtown, PA (US); Chad Glerum, Pennsburg, PA (US); Ty Hessler, Phoenixville, PA (US); Albert Hill, Richboro, PA (US)

(73) Assignee: Globus Medical, Inc., Audubon, PA (US)

( * ) Notice: Subject to any disclaimer, the term of this patent is extended or adjusted under 35 U.S.C. 154(b) by 640 days.

This patent is subject to a terminal disclaimer.

(21) Appl. No.: 17/512,182

(22) Filed: Oct. 27, 2021

(65) Prior Publication Data

US 2022/0047399 A1   Feb. 17, 2022

Related U.S. Application Data

(63) Continuation of application No. 16/515,096, filed on Jul. 18, 2019, now Pat. No. 11,179,242.

(51) Int. Cl.
*A61F 2/44* (2006.01)
*A61F 2/30* (2006.01)

(52) U.S. Cl.
CPC .. *A61F 2/4425* (2013.01); *A61F 2002/30153* (2013.01); *A61F 2002/30329* (2013.01); *A61F 2002/30538* (2013.01); *A61F 2002/30556* (2013.01); *A61F 2002/443* (2013.01)

(58) Field of Classification Search
CPC ....... A61F 2/4425; A61F 2/4455; A61F 2/446
See application file for complete search history.

(56) References Cited

U.S. PATENT DOCUMENTS

| | | | |
|---|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Brian A Dukert

(57) ABSTRACT

A joint spacer has first and second endplates, with each having a bone engaging surface, and at least two cams with an inclined cam surface positioned on an opposite side. First and second slides, each having ramps with an inclined surface are engaged with the cams of the endplate. The first slide has an angled portion at an end, and the second slide has a hinge portion. A threaded shaft has a hinge portion connected to the slide hinge portion, connecting the shaft to the slide, enabling the shaft to pivot. A nut is threaded to the shaft, and can contact and interfere with the angled portion of the first slide to drive the first slide with respect to the second slide. This results in engagement of the cams and ramps to drive the endplates apart to increase the spacer height.

18 Claims, 4 Drawing Sheets

(56) References Cited

U.S. PATENT DOCUMENTS

| | | |
|---|---|---|
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | Jimenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 9,770,343 B2 * | 9/2017 | Weiman ............... A61F 2/4465 |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |

(56) References Cited

U.S. PATENT DOCUMENTS

| | | |
|---|---|---|
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1 | 6/2014 | Seifert et al. |
| 2014/0249630 A1 | 9/2014 | Weiman |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| EP | 3384877 A1 | 10/2018 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |
| WO | 2017066226 A1 | 4/2017 |

\* cited by examiner

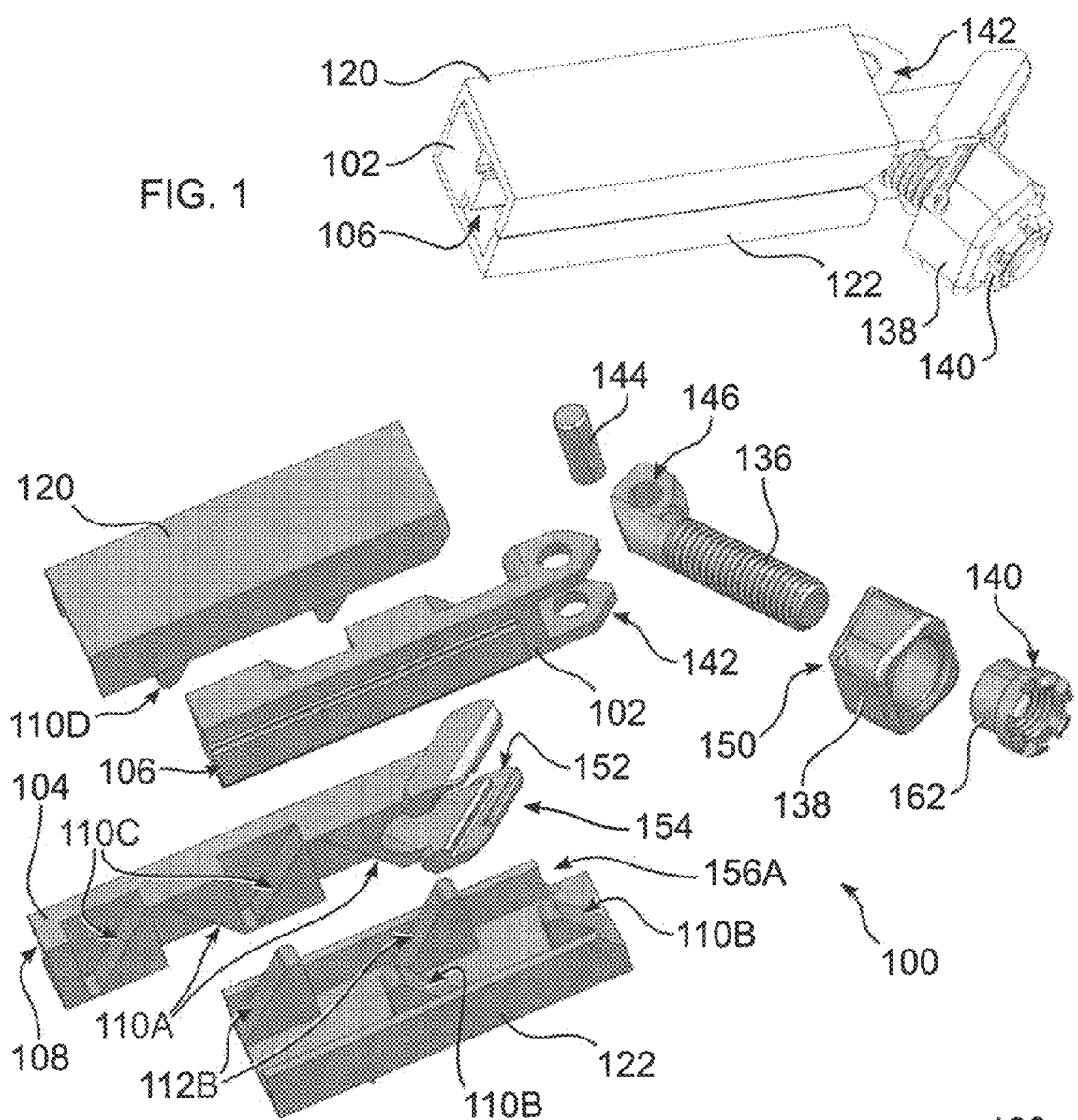
FIG. 1
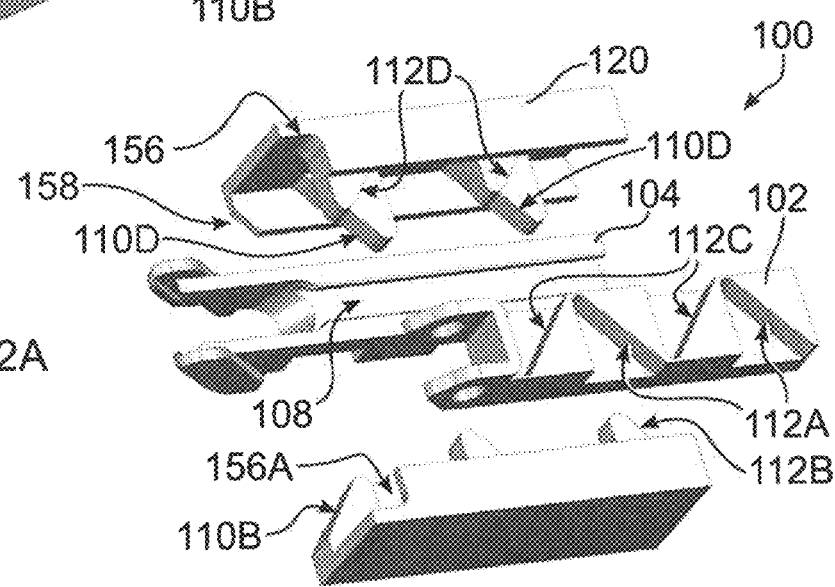
FIG. 2
FIG. 2A

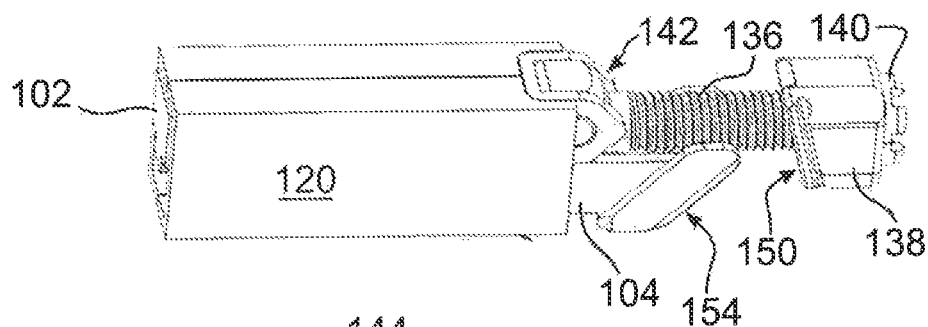
FIG. 3
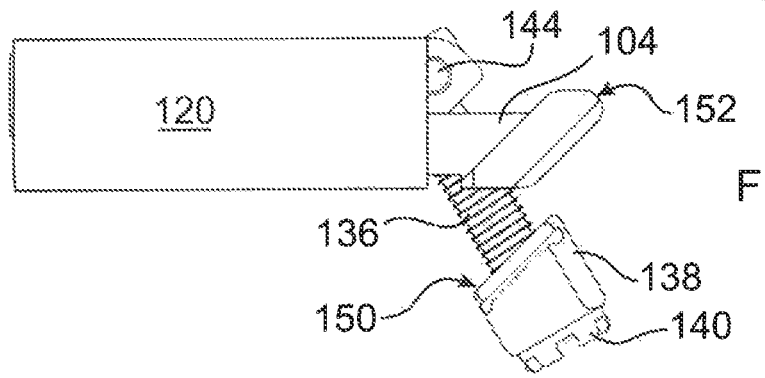
FIG. 4
FIG. 5
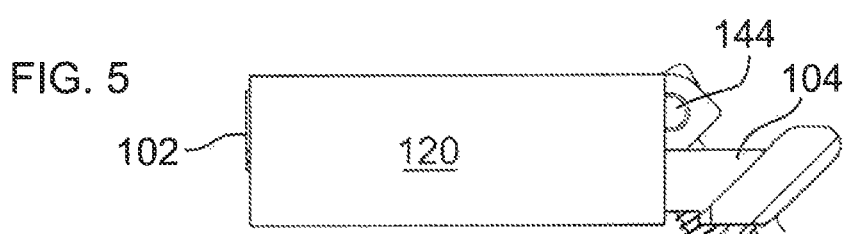
FIG. 6
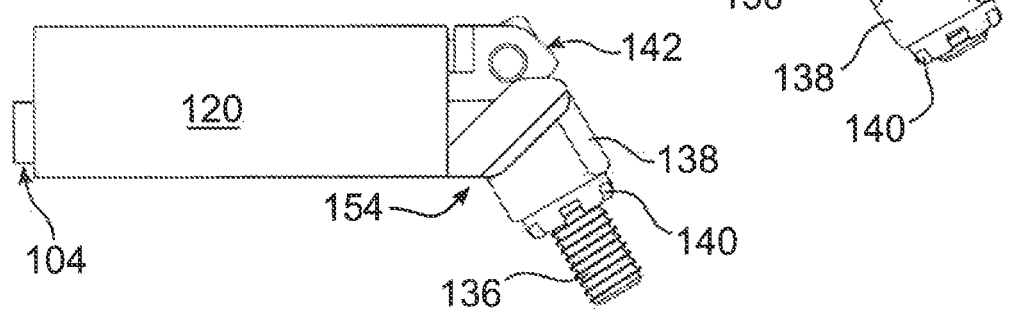
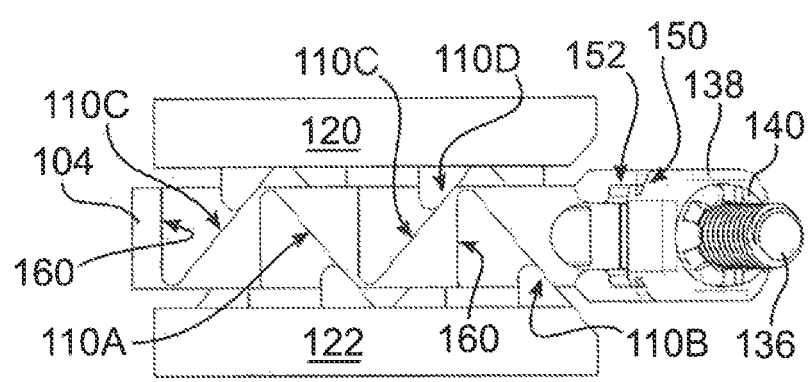
FIG. 7

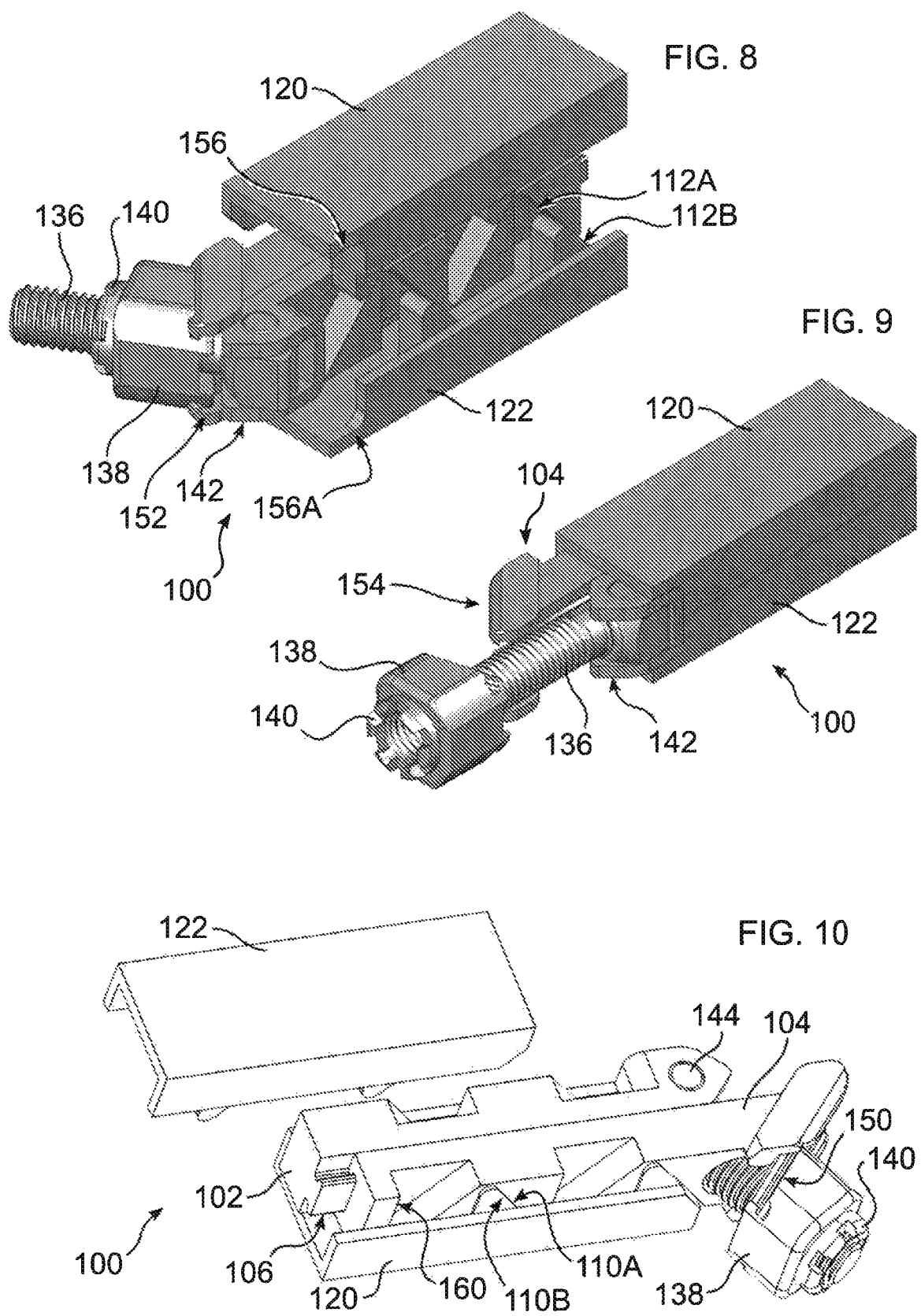

EXPANDING INTERVERTEBRAL IMPLANTS

CROSS-REFERENCE TO RELATED APPLICATION(S)

This patent application is a continuation application of U.S. patent application Ser. No. 16/515,096 filed on Jul. 18, 2019 (published as U.S. Pat. Pub. No. 2021-0015627), the entire disclosure of which is incorporated herein by reference for all purposes.

FIELD OF THE INVENTION

This invention relates to stabilizing adjacent vertebrae of the spine by inserting an intervertebral spacer, and more particularly an intervertebral spacer that is adjustable in height.

BACKGROUND OF THE INVENTION

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan in the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY OF THE INVENTION

In an embodiment of the disclosure, a spacer for separating bones of a joint comprises first and second endplates, each having a bone engaging surface, at least two cams each having an inclined cam surface, the cams positioned on a side opposite to the bone engaging surface; first and second slides, each having at least two ramps each having an inclined surface and each engaged with an inclined cam surface of a cam of an endplate, the first slide having an angled portion at a proximal end, the second slide having a first hinge portion; a threaded shaft having a second hinge portion cooperative with the first hinge portion to connect the shaft to the second slide and to enable the shaft to form a changeable angle with respect to the second slide; a nut threadably engaged with the shaft, the nut forming an interference with the angled portion of the first slide when the nut is threadably advanced upon the shaft, thereby driving the first slide with respect to the second slide causing relative moving engagement of the at least two cams and the at least two ramps to drive the endplates relatively apart and to thereby increase a height of the spacer.

In a variation thereof, the angled portion of the first slide forms a dovetail portion, and the spacer further includes a collar positioned about the shaft and axially slideable along the shaft, the collar contactable by the nut, the collar drivable axially along the shaft by rotation of the nut upon the shaft, and having a dovetail portion mateable with the dovetail portion at the proximal end of the first slide, whereby the interference caused by threading of the nut causes the dovetail portion of the first slide and the dovetail portion of the collar to slide relative to each other in engagement, causing the first slide to slide with respect to the second slide.

In other variations thereof, the nut has an attached sleeve, the collar mountable to the sleeve and radially rotatable upon the sleeve with respect to the shaft; the first and second sliders positioned between the first and second endplates, at least one of the at least two cams of each endplate positioned in contact with one of the at least two ramps of the first slider, at least one of the at least two cams of each endplate positioned in contact with the one of the at least two ramps of the second slider; and/or the at least one cam of each of the first and second endplate includes at least four cams, the at least one ramp of each of the first and second slider includes at least four ramps, two cams of each endplate positioned in contact with two ramps of the first slider, and two cams of each endplate positioned in contact with two ramps of the second slider.

In additional variations thereof, the first and second slides are together bounded by the first and second endplates on top and bottom sides of the first and second slides, the first and second slides are together bounded by eight cams of the first and second endplates on left and right sides of the first and second slides.

In still further variations, the first and second slides are mutually and slideably joined by a mating connection enabling relative sliding along a longitudinal axis; the mating connection is a dovetail connection; and/or the first hinge portion of second slide and the second hinge portion of the threaded shaft together forming a clevis and pin hinge.

In another embodiment of the disclosure, a spacer for separating bones of a joint comprises: first and second endplates, each having a bone engaging surface, at least two cams each having an inclined cam surface, the cams positioned on a side opposite to the bone engaging surface; first and second slides, each having at least two ramps each having an inclined surface and each engaged with an inclined cam surface of a cam of an endplate, the first slide having a dovetail portion at a proximal end, the second slide having a first hinge portion; a threaded shaft having a second hinge portion cooperative with the first hinge portion to connect the shaft to the second slide and to enable the shaft to form a changeable angle with respect to the second slide; a nut threadably engaged with the shaft; a collar positioned about the shaft and axially slideable along the shaft, the collar contactable by the nut, the collar drivable axially along the shaft by rotation of the nut upon the shaft, and having a dovetail portion mateable with the dovetail portion at the proximal end of the first slide; the first slide slideable with respect to the second slide when the dovetail portions of the first slide and the collar are mated, and when the nut is threadably rotated upon the shaft and in contact with the collar, the sliding of the first slide with respect to the second slide causing relative moving engagement of the at least two cams and the at least two ramps to drive the endplates relatively apart and to thereby increase a height of the spacer.

In variations thereof, the nut has an attached sleeve, the collar mountable to the sleeve and radially rotatable upon the sleeve with respect to the shaft; the first and second sliders are positioned between the first and second endplates, at least one of the at least two cams of each endplate positioned in contact with one of the at least two ramps of the first slider, at least one of the at least two cams of each endplate positioned in contact with the one of the at least two ramps of the second slider; and/or the at least one cam of each of the first and second endplate includes at least four cams, the at least one ramp of each of the first and second slider includes at least four ramps, two cams of each endplate positioned in contact with two ramps of the first slider, and two cams of each endplate positioned in contact with two ramps of the second slider.

In further variations thereof, the first and second slides are together bounded by the first and second endplates on top and bottom sides of the first and second slides, the first and second slides together bounded by the eight ramps of the first and second endplates on left and right sides of the first and second slides; the first and second slides are mutually and slideably joined by a mating connection enabling relative sliding along a longitudinal axis; the mating connection is a dovetail connection; and/or the first hinge portion of the second slide and the second hinge portion of the threaded shaft together form a clevis and pin hinge.

In a further embodiment of the disclosure, a method of separating bones of a joint, comprises: inserting a spacer through an opening in Kambin's triangle, the spacer having: first and second endplates, each having a bone engaging surface, at least two cams each having an inclined cam surface, the cams positioned on a side opposite to the bone engaging surface; first and second slides, each having at least two ramps each having an inclined surface and each engaged with an inclined cam surface of a cam of an endplate, the first slide having an angled portion at a proximal end, the second slide having a first hinge portion; a threaded shaft having a second hinge portion cooperative with the first hinge portion to connect the shaft to the second slide and to enable the shaft to form a changeable angle with respect to the second slide; a nut threadably engaged with the shaft, the nut forming an interference with the angled portion of the first slide when the nut is threadably advanced upon the shaft, thereby driving the first slide with respect to the second slide causing relative moving engagement of the at least two cams and the at least two ramps to drive the endplates relatively apart and to thereby increase a height of the spacer; positioning the spacer into a deployment position between vertebral endplates of adjacent vertebrae; the spacer inserted through Kambin's triangle when the endplates are substantially not driven relatively apart, the endplates driven relatively apart by threadably engaging the nut when the spacer is in the deployment position.

In variations thereof, the angled portion of the first slide forming a dovetail portion, the spacer further including a collar positioned about the shaft and axially slideable along the shaft, the collar contactable by the nut, the collar drivable axially along the shaft by rotation of the nut upon the shaft, and having a dovetail portion mateable with the dovetail portion at the proximal end of the first slide, whereby the interference caused by threading of the nut causes the dovetail portion of the first slide and the dovetail portion of the collar to slide relative to each other in engagement, causing the first slide to slide with respect to the second slide; and/or the first and second slides are together bounded by the first and second endplates on top and bottom sides of the first and second slides, the first and second slides together bounded by the cams of the first and second endplates on left and right sides of the first and second slides.

BRIEF DESCRIPTION OF THE DRAWINGS

A more complete understanding of the disclosure, and the attendant advantages and features thereof, will be more readily understood by reference to the following detailed description when considered in conjunction with the accompanying drawings, in which:

FIG. 1 is a perspective view of a spacer implant device of the disclosure, configured to expand upon rotation of a nut;

FIG. 2 is a front view of an exploded view of the device of FIG. 1;

FIG. 2A is a back view of the device of FIG. 2;

FIG. 3 is a side perspective view of a device of the disclosure configured for insertion;

FIG. 4 is a top view of the device of FIG. 1, a threaded shaft angled and in position for engagement with a tool, a collar disengaged from a slide;

FIG. 5 is a top view of the device of FIG. 1;

FIG. 6 is a top view of the device of FIG. 1, a nut tightened to maximally increase a height of the device;

FIG. 7 is a side view of the device of FIG. 6;

FIG. 8 is a back perspective view of the expanded device of FIG. 7;

FIG. 9 is a top perspective view of the device of FIG. 3;

FIG. 10 is a top perspective view of the device of FIG. 5, with an endplate removed;

DETAILED DESCRIPTION OF THE INVENTION

Figure 11:
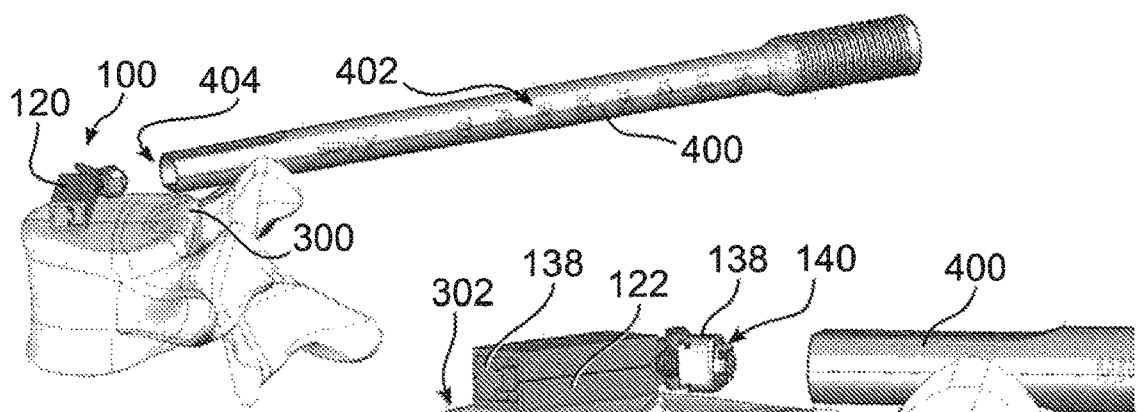
FIG. 11 is a perspective view of an implantation device, the device of FIG. 5 positioned upon a vertebral endplate of a body.

As required, detailed embodiments are disclosed herein; however, it is to be understood that the disclosed embodiments are merely examples and that the systems and methods described below can be embodied in various forms. Therefore, specific structural and functional details disclosed herein are not to be interpreted as limiting, but merely as a basis for the claims and as a representative basis for teaching one skilled in the art to variously employ the present subject matter in virtually any appropriately detailed structure and function. Further, the terms and phrases used herein are not intended to be limiting, but rather, to provide an understandable description of the concepts.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

With reference to the figures, the disclosure provides an expandable spacer/implant or device 100 having an adjustable height. Device 100 is inserted between two adjacent bony surfaces to facilitate separation of the bones, and if desired, to promote the fusion of bony surfaces. Although intended to be useful with any adjacent bony surface in which fusion is desired, device 100 is advantageously applied to insertion between two adjacent vertebral bodies in any section of the spine, including the cervical, thoracic, lumbar, and sacral vertebral sections. More than one device 100 may be implanted within the body, for example between successive or separated vertebrae, or positioned between the same adjacent vertebrae. The use of multiple devices 100 is particularly advantageous for patients whose back pain is not limited to a localized area, or for patients whose localized damage has progressed to other areas of the spine.

Device 100 and methods for its insertion can be used in a treatment protocol for any of a wide variety of conditions in a patient involving diseased or damaged bony structures. The patient can be a human being. Additionally, it is contemplated that device 100 may be useful in veterinary science for any animal having adjacent bony structures to be fused. Devices 100 can expand to roughly twice its fully reduced insertion height. When in this collapsed configuration, device 100 can be inserted into a space through a small incision and narrow pathways, using appropriate minimally-invasive techniques, and can be positioned within the space between adjacent bones, and there expanded to a desired therapeutic height. The incision may be short, for example about one centimeter in length, which is smaller than device 100 in an expanded configuration. If the desired position and/or expansion are not achieved, device 100 can be collapsed, repositioned, and re-expanded in situ.

Although device 100 is exemplified herein for use in the spine, device 100 is contemplated for fusion of any bony structures. While devices 100 are described herein using several varying embodiments, devices 100 are not limited to these embodiments. An element of one embodiment may be used in another embodiment, or an embodiment may not include all described elements.

Interbody devices have been used to provide support and stability in the anterior column of the spinal vertebrae when treating a variety of spinal conditions, including degenerative disc disease and spinal stenosis with spondylolisthesis. Clinical treatment of spinal pathologies with anterior vertebral body interbody devices relies on precise placement of interbodies to restore normal anterior column alignment. Iatrogenic pathologies may result from both the surgical access window to the disc space, failure to precisely place the interbody on hard cortical bone often found on the apophyseal ring of the vertebral body, or failure to precisely control and restore normal anatomical spinal alignment. Device 100 provides for the precise placement of interbody support that both increases interbody contact with hard cortical bone and provides precise control of anterior column alignment while reducing the profile of the access window to the disc space.

More particularly, in order to improve the access profile of the interbody while maximizing cortical bone contact surface area, device 100 enters the disc space with a narrow profile and articulates to increase surface area contact on the anterior apophyseal ring. The orientation and position of the interbody in its final implanted position may be optimized by pre-/intra-op scans or normal population statistics that determine bone mineral density maps of the vertebral body. Robotic and navigation guidance may be used to correctly orient the interbody.

In an embodiment, device 100 can be implanted as follows:

1. A determination is made on final optimal implant location to optimize bone mineral density of the contacted bone/implant interface.

2. Robotic/navigation is used to determine the potential trajectories that will allow for this optimal implant location to be achieved.

3. A cannula is docked on the disc space through Kambin's triangle, or the anatomical area that is bordered by the disc space, exiting nerve root, and traversing nerve root.

4. The expandable interbody is inserted in the non-articulated orientation, which can be seen in FIGS. 3 and 9;

5. The expandable interbody is fully articulated into the articulated orientation that fully maximizes surface contact area with the anterior apophyseal ring of the vertebral body (FIG. 4).

6. The expandable interbody is expanded to precisely restore normal spinal alignment (FIGS. 7-8).

The articulation of the interbody can be accomplished through several methods. In one embodiment, the articulation mechanism consists of an articulation point at the end of a threaded shaft. The articulation mechanism is a hinge joint where the threaded shaft is pinned to the male interior rampslide.

With reference to the drawings, device 100 is expanded using a slide system which causes the separation of endplates 120 and 122, which are each positioned within the body to contact a separate side of a bone joint relative to the other endplate. When positioned within the spine, one endplate will be a superior endplate contacting a more superior vertebra, and the other endplate will be an inferior endplate, contacting a more inferior vertebra. An orientation of device 100 may be determined by the side of the body from which implantation is approached. As will be explained in greater detail elsewhere herein, an actuating shaft 136 forms an angle with respect to the endplates, and it is desired that the shaft lie along the vertebral bone surface, or otherwise does not interfere with movement of the joint or other body tissue.

In particular, and with reference to FIG. 2, device 100 includes first and second slides 102, 104 which are mutually slidingly engaged. In the embodiment shown, each of the first and second slides 102, 104 are provided with a mating dovetail portion 106, 108, respectively which maintains a back-to-back connection and orientation between slides 102, 104 as they are slid along their longitudinal axes with respect to each other. A length or longitudinal axis extends along a direction of insertion of device 100, described further elsewhere herein. A height of device 100 extends transverse to the longitudinal axis.

Slides 102 and 104 cooperate to cause endplates 120, 122 to change a distance from each other when slides 102 and 104 are slid relative to each other. With reference to FIG. 2, slide 104 forms one or more ramps 110A which each engage a mating cam 110B, having a surface which corresponds to ramp 110A, on endplate 122. Likewise, and with additional reference to FIG. 2A, slide 104 forms one or more ramps 110C which each engage a mating cam 110D on endplate 120. In a similar fashion, slide 102 forms one or more ramps 112A which each engage a mating cam 112B on endplate 122, and one or more ramps 112C which each engage a mating cam 112D on endplate 120.

Cams 110B and 112B are angled in opposite directions, and cams 110D and 112D are likewise angled in opposite directions. In this manner, as slides 102 and 104 are moved in opposing directions towards a more overlapping relationship, cams 110B, 112B, 110D, and 112D slide along and up ramps 110A, 112A, 110C, and 112C, respectively, driving endplates 120, 122 apart. Similarly, as slides 102 and 104 are moved in opposing directions towards a less overlapping relationship, cams 110B, 112B, 110D, and 112D slide along and down ramps 110A, 112A, 110C, and 112C, respectively, enabling endplates 120, 122 to move together, for example by pressure applied by body tissue. Cams 110B, 112B, 110D, and 112D each have an inclined cam surface which corresponds to the inclination of a surface of a mating ramp 110A, 112A, 110C, and 112C.

Dovetail portions 106 and 108 on slides 102 and 104 cooperate to maintain contact between slides 102 and 104 during relative movement along the longitudinal axis. This contributes to stability and reliability of device 100. In an alternative embodiment, dovetail portions 106 and 108 do not prevent slides 102 and 104 from separating along a direction transverse to the longitudinal axis. For example, dovetail portions 106 and 108 can have the form of a protrusion and a groove. In a further embodiment, dovetail portions 106 and 108 are absent, and slides 102 and 104 are confined in movement by being bounded by cams 110B, 112B, 110D, and 112D, and through a mutual connection established through dovetail surfaces 150 and 152 of collar 138 and the proximal end 154 of slide 104. It should further be understood that while the dovetail examples in the drawings illustrate a male component on one part, and a female component on another part, the relative placement of these components can be reversed.

A vertical surface 160 (FIGS. 7 and 10) can be formed adjacent to any or all of ramps 110A, 112A, 110C, and 112C to provide room for entry of cams 110B, 112B, 110D, and 112D, and to further prevent relative movement of slides 102, 104 when device 100 has been reduced to the lowest desired height profile.

In addition, when slides 102, 104 are slid to be relatively less overlapping along a longitudinal direction, cams 110B, 112B, 110D, and 112D are more completely overlapping and nesting against ramps 110A, 112A, 110C, and 112C, so that endplates 120, 122 are disposed more closely to each other, reducing an overall height profile of device 100. As slides 102, 104 are displaced to be relatively more overlapping, cams 110B, 112B, 110D, and 112D are less completely overlapping/nesting against ramps 110A, 112A, 110C, and 112C, so that endplates 120, 122 are disposed farther from each other, increasing an overall height profile of device 100.

With further reference to FIG. 2 in particular, a series of components connected to slides 102 and 104 enable the aforedescribed relative sliding displacement of slides 102, 104. More particularly, a threaded shaft 136 is connected at one end of slide 102, and a collar 138, driven by a nut 140 engaged with shaft 136, is connected to slide 104. Collar 138 is free to rotate and slide along shaft 136, and is pushed along a longitudinal axis of shaft 136 by the rotation of nut 140. Shaft 136 is pivotably engaged with slide 102 by a pin 144 which passes through a clevis 142 mounted to an end of slide 102, and through a bore 146 formed in an end of shaft 136. Collar 138 includes a collar dovetail portion 150, and slide 104 includes a mating slide dovetail end portion 152 disposed at a proximal end 154. As shown in the drawings, collar 138 is slidable about a sleeve 162 (FIG. 2) associated with nut 140. In alternative embodiments, sleeve 162 is omitted, or collar 138 forms a different engagement with nut 140.

Shaft 136 can be pivotally connected to slide 102 by means other than a clevis and pin, for example through any known hinge mechanism, including barrel, flush, living, piano, gate, butt, butterfly, pivot, or spring hinge, as examples, although other hinge structures can be used which enable shaft to form a changeable angle with respect to slide 102, and which can be formed in a space efficient manner.

Endplates 120, 122 can be provided with cutout portions 156, 156A (FIGS. 2A and 8), respectively, to provide room for clevis 142. Similarly, other areas of endplates 120, 122 can be provided with a relief 158 (FIG. 2A) or removed material to accommodate a cam, as shown at 110B in FIG. 2, or to provide room for other structures when device 100 is at various height configurations, as needed.

In an insertion orientation, collar 138 is disengaged from slide dovetail end portion 152, and shaft 136 is pivoted about pin 144 to be longitudinally aligned with slides 102, 104, as shown in FIG. 3. In this configuration, which has the smallest end-on profile, device 100 can be inserted into the body to an implantation site through a correspondingly small opening with a minimum of tissue disruption. Specifically, when collar 138 is disengaged, endplates can be urged towards each other, longitudinally offsetting slides 102, 104, while producing a longer profile along the longitudinal axis, but the smallest height profile. In an embodiment, the height profile is not greater than the width and thickness of stacked endplates 120 and 122. As can be seen in FIGS. 1, 3 and 9-10, slides 102, 104 nest completely within endplates 120, 122.

While device 100 is positioned within the body, shaft 136 is pivoted about pin 144, and collar 138 is rotated, so that collar dovetail portion 150 is aligned parallel with slide dovetail end portion 152, as can be seen in FIG. 4. Collar 138 can then be driven along shaft 136 by rotation of nut 140, until collar dovetail portion 150 is aligned with slide dovetail end portion 152, after which the respective dovetail portions can be mated, as can be seen in FIGS. 1 and 5. Nut 140 can then be threaded further along shaft 136, causing collar 138 to advance along shaft 136, to the point of creating contact between collar 138 and slide 102, thereafter, as nut 140 is turned further, this contact and interference causes dovetail portions 150 and 152 to slide relative to each other, thereby driving slide 104 relative to slide 102, through the sliding connection of dovetail portions 150, 152. Accordingly, as shaft 136 is affixed to slide 102, and collar 138 is affixed to slide 104, advancement of collar 138 along shaft 136 causes slides 102 and 104 to move in opposite directions, resulting in a change of height of device 100 as described above.

Endplates 120 and 122 each have parallel sets of spaced apart cams (two each of 110D, 112D, 110B, 112B), which cooperate with a matching number of ramps (two each of 110A, 110C, 112A, 112C) on slides 102, 104, to create stability with respect to side-to-side and end-to-end rocking, and which are matched in size to produce relatively parallel movement of endplates 120, 122 as they are moved closer together and farther apart.

In one embodiment of the disclosure, dovetail portions 150, 152, and collar 138 are not present. In this embodiment, nut 140 bears directly upon an end of slide 104. In lieu of a dovetail portion 150, slide 104 can be provided with a ramped surface at a proximal end of slide 104, and in one variation the ramp has a similar angle as dovetail 150. In this embodiment, shaft 136 is maintained at an angle at which nut 140 bears upon this angled proximal end. As nut 140 is rotated, an interference is created between the nut and/or a collar if present and slide 104, causing slide 104 to be driven with respect to slide 102 as otherwise described herein.

Advantages of the disclosure include, at least:

1. A small insertion profile: the disclosure enables, for example, an 8.5 mm insertion profile into the disc space, reducing the required skin, fascia, muscle, and ligamentous disruption. Smaller profiles can be achieved, including profiles as small as 6 mm, for example, or profiles substantially larger than 8.5 mm.

2. Controlled lordosis: the disclosure enables controlled lordosis through placement of device 100 in an articulated position in the disc space. With the spacer placed horizontally across the disc space, and due to the fact that the spacer has a relatively small depth, the spacer can be used as a fulcrum to increase lordosis as it is expanded. It is generally accepted that placing the spacer on the anterior apophyseal ring provides the most leverage for continuously increasing lordosis as it is expanded in height. However, more posterior placement can also be utilized as this can allow for increased anterior height when leveraging using the same height spacer. Alternatively, two devices 100 can be placed between the same vertebrae, one in the anterior aspect of the vertebral body and one in the posterior aspect of the vertebral body, to further control and adjust sagittal balance by then allowing independent expansion of the anterior and posterior aspects of the vertebral body.

3. Reduced endplate disruption: due to the ability of device 100 to expand a correct, therapeutic extent in situ, the disclosure reduces the need for traditional trialing through the insertion of interbody implants of various sizes, the latter potentially causing or contributing to vertebral endplate disruption and further trauma to the body.

Figure 12:
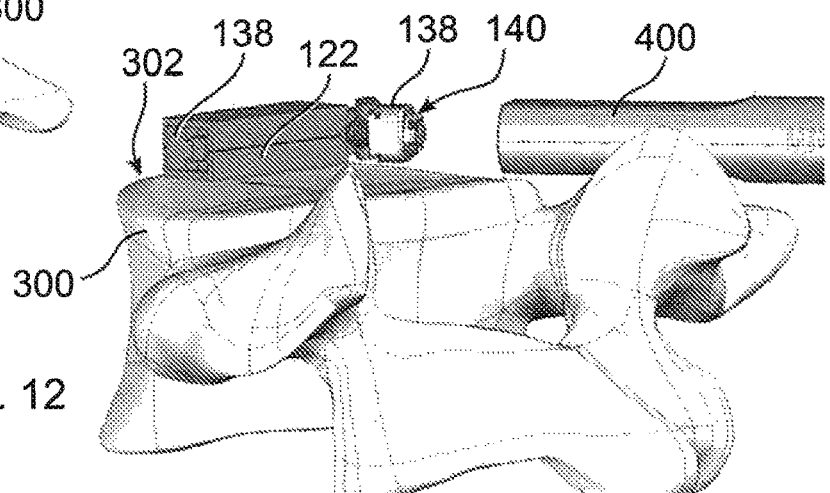
FIG. 12 is a detailed view of the device and vertebral endplate of FIG. 11.

With reference to FIGS. 11-12, a driving tool 400 forms a cannula. Indicia 402 indicates an insertion depth of tool 400 into the body. Positioning is carried out using imaging, and can further be carried out using a robotics system. The bore 404 of tool 400 enables the insertion of surgical instruments in order to cut, excise, or cauterize body tissue, and to otherwise facilitate a surgical procedure to implant device 100. Bore 404 is further sized to enable passage of device 100. To minimize the required size of bore 404, device 100 is configured in the smallest height profile, and with threaded shaft 136 disengaged from slide 104 and extending linearly along a longitudinal axis of device 100, as shown in FIGS. 3 and 9.

Figure 13:
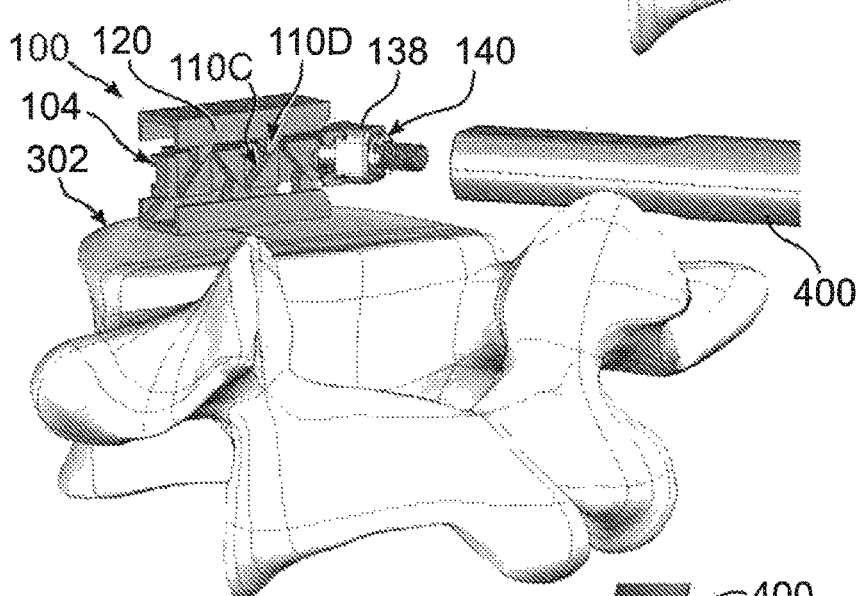
FIG. 13 is a detailed view of the device of FIG. 12, the nut advanced and the device expanded in height.
Figure 14:
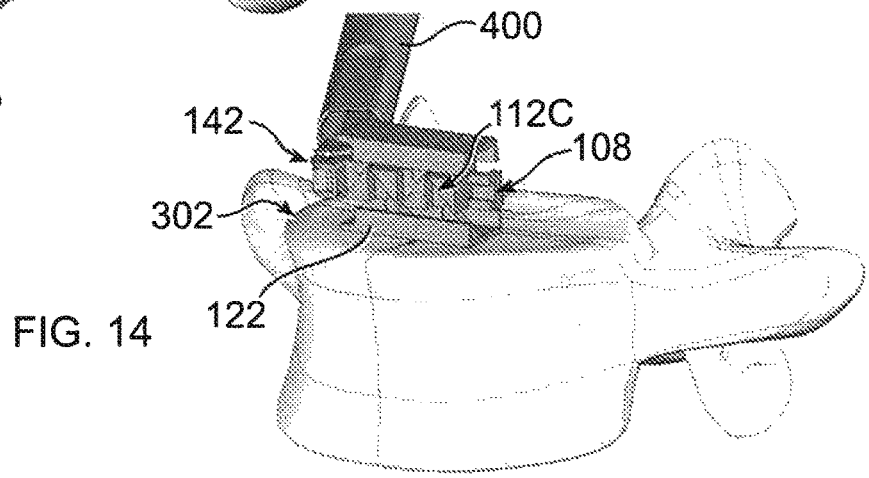
FIG. 14 is a back view of the device of FIG. 13.

After device 100 exits tool 400 within the body, it may be manipulated into a position upon the vertebral endplate 300, for example upon the apophyseal ring 302, using surgical tools passed through tool 400. Additionally, shaft 136 can be angled to enable engagement of dovetail portions 150, 152, coupling slides 102 and 104 as described elsewhere herein. After dovetail portions 150, 152 are engaged, a driving tool (not shown) can be passed through tool 400 and engaged with nut 140 to rotate nut 140, causing relative sliding of slides 102, 104, and expanding a height of device 100, as can be seen in FIGS. 13-14. At a later date, if needed, tool 400 can be reinserted into the body to change reposition device 100, change a height of device 100 by rotating nut 140, and/or device 100 can be removed from the body if therapeutically beneficial.

Different devices 100 may include ramps 110A, 110C, 112A, 112C and/or cams 110B, 110D, 112B, 112D of differing height and length relative to other devices 100, to enable expansion at different rates or extents, as indicated for therapeutic treatment. Fewer or a greater number of ramps and/or cams can be provided. Endplates 102, 104 may additionally, or alternatively, be resilient, so that they may conform to bony surfaces, forming a more stable support platform. Accordingly, endplates 102, 104 can be fabricated from a polymeric material, a naturally resilient material, or a resilient metal, for example a shape memory alloy, or any other resilient biocompatible material of sufficient strength and durability for separating bones within the body.

Device 100 can be inserted at a contracted height transforaminally, for example, and are capable of articulating into anterior placement. Once placement is achieved, device 100 is capable of expanding for disc height restoration. Additionally, device 100 can be positioned anteriorly, and can be expanded through a continuous range to provide axial balance and greater endplate contact area. Additionally, device 100 enables superior sagittal correction, through the use of a relatively smaller insertion window, decreasing the need for bone damage. Thus, device 100 provides the benefits of an ALIF device through a familiar posterior approach, decreasing surgery time and associated blood loss, as well as eliminating the need for an access surgeon.

In accordance with the disclosure, during implantation of intervertebral spacers from a posterior approach, there is a need to avoid damaging nerve roots. A prior art spacer dimensioned to separate bones can block a view of nerve roots as it is inserted, and due to its large size, poses a greater risk of contacting nerve roots during insertion into the body. As a result, the medical practitioner must more often retract nerve roots, with attendant danger of tissue damage. Devices 100 of the disclosure form a smaller dimension during implantation, relative to a final dimension for spacing bones. Accordingly, nerve roots can be visualized and avoided during insertion, and nerve root manipulation can be avoided or minimized.

As devices 100 of the disclosure can be articulated during implantation, they can be inserted between bones by being passed through a minimally invasive entry, for example through an incision approximating the smallest collapsed dimension, for example transverse to the longitudinal dimension. This enables exceptional anterior placement without impaction, as well as facilitating implantation from other approaches. Devices 100 of the disclosure further develop a good bone contact area, as an implant with a larger footprint may be inserted through a reduced size incision, due to the overall dimensions of device 100 being reduced during insertion.

Devices 100 of the disclosure enable a continuous expansion and distraction over a range of displacements according to predetermined dimensions of a specific spacer design. This provides the ability to distract vertebral bodies or other bones to a desired height or separation. Endplates 120, 122 can be shaped to form planes or surfaces which converge relative to each, to provide for proper lordosis, and can be provided with openings 190 through which bone may grow, and into which bone graft material may be placed. Devices 100 of the disclosure may be used to distract, or force bones of a joint apart, or may be used to maintain a separation of bones created by other means, for example by a retractor. Endplates may additionally be curved to conform to the surface of body tissue, for example the surface of cortical bone, of the vertebra to be contacted, for improved fixation and load bearing.

Devices 100 of the disclosure may be further secured in connection with the body by passage of elongated fasteners through an endplate 120, 122. A blocking mechanism can be used to prevent backing out of an elongated fastener.

Devices 100 of the disclosure may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; polymers, including for example, PEEK or ultra high molecular weight polyethylene (UHMWPE); and ceramics. There are many other biocompatible materials which may be used, including other plastics and metals, as well as fabrication using living or preserved tissue, including autograft, allograft, and xenograft material.

Portions or all of device 100 may be radiopaque or radiolucent, or materials having such properties may be added or incorporated into device 100 to improve imaging of the device during and after implantation.

Devices 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of devices 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of devices 100 of the disclosure. For example, polymeric portions can be formed with PEEK-OPTIMA, which is radiolucent, whereby bony ingrowth may be observed. Other polymeric materials with suitable flexibility, durability, and biocompatibility may also be used.

In accordance with the invention, implants of various sizes may be provided to best fit the anatomy of the patient. Components of matching or divergent sizes may be assembled during the implantation procedure by a medical practitioner as best meets the therapeutic needs of the patient, the assembly inserted within the body using an insertion tool. Devices 100 of the invention may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

Expanded implant heights, for use in the cervical vertebrae for example, may typically range from 7 mm to 12 mm, but may be larger or smaller, including as small as 5 mm, and as large as 16 mm, although the size is dependent on the patient, and the joint into which an implant of the invention is to be implanted. Devices 100 may be implanted within any level of the spine, and may also be implanted in other joints of the body, including joints of the hand, wrist, elbow, shoulder, hip, knee, ankle, or foot.

In accordance with the invention, a single device 100 may be used, to provide stabilization for a weakened joint or joint portion. Alternatively, a combination of two, three, or more of any of device 100 may be used, at a single joint level, or in multiple joints. Moreover, implants of the disclosure may be combined with other stabilizing means.

Additionally, devices 100 of the disclosure may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

Any surface or component of a device 100 of the disclosure may be coated with or impregnated with therapeutic agents, including bone growth, healing, antimicrobial, or drug materials, which may be released at a therapeutic rate, using methods known to those skilled in the art.

Devices of the disclosure provide for adjacent vertebrae to be supported during flexion/extension, lateral bending, and axial rotation. In one embodiment, device 100 is indicated for spinal arthroplasty in treating skeletally mature patients with degenerative disc disease, primary or recurrent disc herniation, spinal stenosis, or spondylosis in the lumbosacral spine (LI-SI). Degenerative disc disease is advantageously defined as discogenic back pain with degeneration of the disc confirmed by patient history and radiographic studies, with or without leg (radicular) pain. Patients are advantageously treated, for example, who may have spondylolisthesis up to Grade 1 at the involved level. The surgery position device 100 may be performed through an Anterior, Anterolateral, Posterolateral, Lateral, or any other approach.

In a typical embodiment, devices 100 of the disclosure have an uncompressed height, before insertion, of 7 to 13 mm, and may advantageously be provided in cross-sections of 8×22, 8×26, 8×30, 8×34, 10×27 mm, 12×32 mm and 12×37 mm, with 4, 8, 12, 15, 20, 25, or 30 degree lordotic angles, although these are only representative sizes, and substantially smaller or larger sizes can be therapeutically beneficial. In one embodiment implants in accordance with the instant disclosure are sized to be inserted using an MIS approach, for example using a reduced incision size, for example less than about 5 cm, and advantageously less than about 1 cm, with fewer and shorter cuts through body tissue. Device 100 may advantageously be used in combination with other known or hereinafter developed forms of stabilization or fixation, including for example rods and plates, or intradiscal fixation, potentially connecting device 100 to one or more of the adjacent vertebrae.

Devices 100 of the disclosure can be inserted into the body, advantageously in a contracted or non-expanded configuration, through a transforaminal approach, and can articulate in attachment to an inserter tool, for example as shown in FIGS. 11-14 or another tool, for example for anterior placement. Once placement is achieved, device 100 is capable of expanding for disc height restoration. To maintain an engagement device 100 and an insertion tool, a driving end (not shown) of the tool can be engaged with device 100.

All references cited herein are expressly incorporated by reference in their entirety. There are many different features to the present disclosure and it is contemplated that these features may be used together or separately. Unless mention was made above to the contrary, it should be noted that all of the accompanying drawings are not to scale. Thus, the disclosure should not be limited to any particular combination of features or to a particular application of the disclosure. Further, it should be understood that variations and modifications within scope of the disclosure might occur to those skilled in the art to which the disclosure pertains. Accordingly, all expedient modifications readily attainable by one versed in the art from the disclosure set forth herein that are within the scope of the present disclosure are to be included as further embodiments of the present disclosure.

What is claimed is:

1. A spacer for separating bones of a joint, the spacer comprising:
   a first endplate;
   a second endplate;
   a first slide configured to engage the first and second endplate, wherein the first slide has an angled portion at a proximal end;
   a second slide configured to engage the first and second endplate, wherein the second slide has a first hinge portion;
   a shaft having a second hinge portion configured to engage the first hinge portion, wherein the shaft is configured to form a changeable angle with respect to the second slide; and
   a nut engaged with the shaft and configured to engage the angled portion of the first slide, wherein when the nut is advanced upon the shaft the first slide moves with respect to the second slide causing the endplates to move relatively apart and to thereby increase a height of the spacer,
   wherein the first and second slides are mutually and slideably joined by a mating connection enabling relative sliding along a longitudinal axis.

2. The spacer of claim 1, the angled portion of the first slide forming a dovetail portion, the spacer further including a collar positioned about the shaft and axially slideable along the shaft, the collar contactable by the nut, the collar drivable axially along the shaft by rotation of the nut upon the shaft, and having a dovetail portion mateable with the dovetail portion at the proximal end of the first slide, whereby an interference caused by threading of the nut causes the dovetail portion of the first slide and the dovetail portion of the collar to slide relative to each other in engagement, causing the first slide to slide with respect to the second slide.

3. The spacer of claim 2, the nut having an attached sleeve, the collar mountable to the sleeve and radially rotatable upon the sleeve with respect to the shaft.

4. The spacer of claim 1, the first and second slides positioned between the first and second endplates.

5. The spacer of claim 4, wherein the first and second endplates includes one or more cams, each cam configured to engage a ramp on at least one of the first and second slides.

6. The spacer of claim 5, the first and second slides together bounded by the first and second endplates on top and bottom sides of the first and second slides.

7. The spacer of claim 1, the mating connection being a dovetail connection.

8. The spacer of claim 1, the first hinge portion of second slide and the second hinge portion of the threaded shaft together forming a clevis and pin hinge.

9. The spacer of claim 1, wherein the shaft is threaded.

10. A method of separating bones of a joint, comprising:
    inserting a spacer through an opening in Kambin's triangle, the spacer having:
      a first endplate;
      a second endplate;
      a first slide configured to engage the first and second endplate, wherein the first slide has an angled portion at a proximal end;
      a second slide configured to engage the first and second endplate, wherein the second slide has a first hinge portion;
      a shaft having a second hinge portion configured to engage the first hinge portion, wherein the shaft is configured to form a changeable angle with respect to the second slide; and
      a nut engaged with the shaft and configured to engage the angled portion of the first slide, wherein when the nut is advanced upon the shaft the first slide moves with respect to the second slide causing the endplates to move relatively apart and to thereby increase a height of the spacer;
    positioning the spacer into a deployment position between vertebral endplates of adjacent vertebrae;
    the spacer inserted through Kambin's triangle when the endplates are substantially not driven relatively apart, the endplates driven relatively apart by threadably engaging the nut when the spacer is in the deployment position,
    wherein the first and second slides are mutually and slideably joined by a mating connection enabling relative sliding along a longitudinal axis.

11. The method of claim 10, the angled portion of the first slide forming a dovetail portion, the spacer further including a collar positioned about the shaft and axially slideable along the shaft, the collar contactable by the nut, the collar drivable axially along the shaft by rotation of the nut upon the shaft, and having a dovetail portion mateable with the dovetail portion at the proximal end of the first slide, whereby an interference caused by threading of the nut causes the dovetail portion of the first slide and the dovetail portion of the collar to slide relative to each other in engagement, causing the first slide to slide with respect to the second slide.

12. The method of claim 11, the nut having an attached sleeve, the collar mountable to the sleeve and radially rotatable upon the sleeve with respect to the shaft.

13. The method of claim 10, the first and second slides positioned between the first and second endplates.

14. The method of claim 13, wherein the first and second endplates includes one or more cams, each cam configured to engage a ramp on at least one of the first and second slides.

15. The method of claim 14, the first and second slides together bounded by the first and second endplates on top and bottom sides of the first and second slides.

16. The method of claim 10, the mating connection being a dovetail connection.

17. The method of claim 10, the first hinge portion of second slide and the second hinge portion of the threaded shaft together forming a clevis and pin hinge.

18. The method of claim 10, wherein the shaft is threaded.

* * * * *